(12) United States Patent
Korth et al.

(10) Patent No.: US 7,019,160 B2
(45) Date of Patent: *Mar. 28, 2006

(54) PROCESS FOR THE PREPARATION OF (MERCAPTOORGANYL)ALKOXYSILANES

(75) Inventors: Karsten Korth, Grenzach-Wyhlen (DE); Philipp Albert, Lörrach (DE); Ingo Kiefer, Schopfheim (DE)

(73) Assignee: Degussa AG, Düsseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/980,859

(22) Filed: Nov. 4, 2004

(65) Prior Publication Data
US 2005/0124822 A1     Jun. 9, 2005

(30) Foreign Application Priority Data
Nov. 6, 2003   (DE) ............................... 103 51 736

(51) Int. Cl.
*C07F 7/04* (2006.01)
(52) U.S. Cl. .................................... 556/429
(58) Field of Classification Search ................ 556/429
See application file for complete search history.

(56) References Cited

U.S. PATENT DOCUMENTS

| 3,590,065 | A | 6/1971 | Rakus et al. .......... 260/448.8 R |
| 3,849,471 | A | 11/1974 | Omietanski et al. .. 260/448.2 E |
| 4,012,403 | A | 3/1977 | Mui ..................... 260/448.8 R |
| 4,082,790 | A | 4/1978 | Speier ................. 260/448.8 E |
| 5,107,009 | A | 4/1992 | Rauleder et al. ............. 556/429 |
| 5,840,952 | A | 11/1998 | Kudo et al. ................. 556/429 |

FOREIGN PATENT DOCUMENTS

| DE | 2035 619 | 2/1971 |
| EP | 0 018 094 B1 | 6/1982 |
| EP | 0 471 164 B1 | 11/1995 |
| GB | 1102251 | 2/1968 |

OTHER PUBLICATIONS

Abstract for Reference B2 above.
Abstract for Reference B3 above.

*Primary Examiner*—Samuel Barts
(74) *Attorney, Agent, or Firm*—Michael A. Sanzo; Fitch, Even, Tabin & Flannery

(57) ABSTRACT

The present invention relates to a process for the preparation of (mercaptoorganyl)-alkoxysilanes by reacting an alkali metal sulfide with a mixture of (haloorganyl)alkoxysilane and (haloorganyl)halosilane in an alcohol with the exclusion of air and under elevated pressure.

10 Claims, No Drawings

PROCESS FOR THE PREPARATION OF (MERCAPTOORGANYL)ALKOXYSILANES

CROSS REFERENCE TO RELATED APPLICATIONS

The present application claims priority to German application DE 103 51 736.7, filed on Nov. 6, 2003, the contents of which is hereby incorporated by reference.

FIELD OF THE INVENTION

The invention relates to a process for the preparation of (mercaptoorganyl) alkoxysilanes.

BACKGROUND OF THE INVENTION

Mercaptoalkylsilanes may be prepared in a one-step process by reacting (haloorganyl)alkoxysilane compounds with thiourea and ammonia (DE AS 2035619). This method has the disadvantage that long batch times (more than 24 hours) are required to achieve economically acceptable conversion rates. The yields that are achievable with this procedure are variable and typically reach values of only 75 to 80%. In addition, guanidine hydrochloride is formed and this must be separated and disposed of at additional expense.

Mercaptoalkylsilanes may also be prepared in which mercaptosilanes are formed by hydrogenation of thiopropionic acid amide silanes under pressure (EP 0018094) or by hydrogenation of cyanoalkylsilane compounds in the presence of elemental sulfur or hydrogen sulfide (U.S. Pat. No. 4,012,403). Both processes have the disadvantage of poor yield.

U.S. Pat. No. 3,849,471 discloses the preparation of mercaptosilanes by reaction of (haloorganyl)alkoxysilane compounds with hydrogen sulfide in the presence of ethylene-diamine and large amounts of heavy metal sulfides. A disadvantage of this process is the formation of various secondary products which must be separated out. The process can be improved by eliminating the diamines and reacting the starting silanes with hydrogen sulfide in the presence of ammonia, primary, secondary or tertiary amines, and, optionally, in the presence of polar, protic or aprotic media (U.S. Pat. No. 4,082,790). However, in order to achieve the required reaction temperatures, the process must be carried out in high-pressure autoclaves. If the reactions are carried out in the absence of polar media, long reaction times are needed to achieve acceptable conversion rates. Moreover, the metered addition and handling of highly toxic $H_2S$ on an industrial scale is undesirable, expensive and requires rigorous safety precautions.

Mercaptosilanes may also be formed by the reaction of alkali hydrogen sulfides with (haloalkyl)alkoxysilanes in a methanolic medium (GB 1 102 251). This procedure has the disadvantage that an extraordinarily long reaction time (96 hours) is required to achieve high conversion rates and the yield achieved is unsatisfactory.

(Mercaptoalkyl)alkoxysilanes may be produced by reacting alkali hydrogen sulfide with suitable (haloalkyl)alkoxysilanes in the presence of a 10–100% molar excess of $H_2S$ (U.S. Pat. No. 5,840,952). However, on an industrial scale, this process has the disadvantage that highly toxic $H_2S$ has to be stored, metered and handled. In addition, the process is carried out in two stages and this results in a diminished space-time yield.

Another process for preparing (mercaptoalkyl)alkoxysilanes is by reacting (haloalkyl)alkoxysilanes with alkali hydrogen sulfide (NaSH) in polar, aprotic solvents (EP 0 471 164). One disadvantage of this process is that it uses a large quantity, at least 50 vol. %, of solvent, and this may be highly toxic, e.g., dimethylformamide. In addition, the high boiling-point of solvents such as dimethylformamide makes the later distillative reprocessing and purification of the reaction products more difficult.

DESCRIPTION OF THE INVENTION

The objective of the present invention is to provide a process for making (mercaptoorganyl)alkoxysilanes in which no gaseous raw materials are used and high space-time yields in the reaction of the (haloorganyl)silanes are achieved while avoiding the metered addition and handling of highly toxic hydrogen sulfide or toxic dimethylformamide. The process involves reacting an alkali metal sulfide with a mixture of (haloorganyl)alkoxy-silane and (haloorganyl)halosilane in an alcohol with the exclusion of air and under elevated pressure. The term "under elevated pressure" means an excess pressure of from 0.1 to 10 bar, and preferably from 1 to 7 bar, above normal pressure.

The (mercaptoorganyl)alkoxysilanes made by the process include compounds of the general formula I:

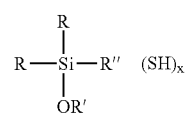

wherein:
the substituents R are identical or different and are: a $C_1$–$C_8$ alkyl (preferably $CH_3$); an alkenyl (preferably a $C_2$–$C_{12}$ alkenyl); an aryl (preferably a $C_6$–$C_{10}$ aryl); an aralkyl (preferably a $C_7$–$C_{16}$ aralkyl); or a group OR';
the substituents R' are identical or different and are: a $C_1$–$C_{24}$ (preferably $C_1C_4$ or $C_{12}$–$C_{18}$ branched or unbranched monovalent alkyl or alkenyl group; an aryl group (preferably a $C_6$–$C_{10}$ aryl group), or an aralkyl group (preferably a $C_7$–$C_{16}$ aralkyl group);
R" is a branched or unbranched, saturated or unsaturated, aliphatic, aromatic or mixed aliphatic/aromatic divalent $C_1$–$C_{30}$ hydrocarbon group which is optionally substituted by F, Cl, Br, I, $NH_2$ or NHR'; and
x is 1–3.

When x=1, R" is preferably —$CH_2$—, —$CH_2CH_2$—, —$CH_2CH_2CH_2$—, —$CH_2CH_2CH_2CH_2$—, —$CH(CH_3)$—, —$CH_2CH(CH_3)$—, —$CH(CH_3)CH_2$—, —$C(CH_3)_2$—, —$CH(C_2H_5)$—, —$CH_2CH_2CH(CH_3)$—, —$CH_2CH(CH_3)CH_2$—, or

When x=2, R" is preferably CH, —CH—$CH_2$, —$CH_2$—CH, C—$CH_3$, —CH—$CH_2$—$CH_2$, —CH—CH—$CH_3$ or —$CH_2$—CH—$CH_2$.

Preferred (mercaptoorganyl)alkoxysilanes of formula I are:
3-mercaptopropyl(trimethoxysilane);
3-mercaptopropyl(triethoxysilane);

3-mercaptopropyl(diethoxymethoxysilane);
3-mercaptopropyl(tripropoxysilane);
3-mercaptopropyl(dipropoxymethoxysilane);
3-mercaptopropyl(tridodecanoxysilane);
3-mercaptopropyl(tritetradecanoxysilane);
3-mercaptopropyl(trihexadecanoxysilane);
3-mercaptopropyl(trioctadecanoxysilane);
3-mercaptopropyl(didodecanoxy)tetradecanoxysilane;
3-mercaptopropyl(dodecanoxy)tetradecanoxy(hexadecanoxy)silane;
3-mercaptopropyl(dimethoxymethylsilane);
3-mercaptopropyl(methoxydimethylsilane);
3-mercaptopropyl(diethoxymethylsilane);
3-mercaptopropyl(ethoxydimethylsilane);
3-mercaptopropyl(dipropoxymethylsilane);
3-mercaptopropyl(propoxydimethylsilane);
3-mercaptopropyl(diisopropoxymethylsilane);
3-mercaptopropyl(isopropoxydimethylsilane);
3-mercaptopropyl(dibutoxymethylsilane);
3-mercaptopropyl(butoxydimethylsilane);
3-mercaptopropyl(diisobutoxymethylsilane);
3-mercaptopropyl(isobutoxydimethylsilane);
3-mercaptopropyl(didodecanoxymethylsilane);
3-mercaptopropyl(dodecanoxydimethylsilane);
3-mercaptopropyl(ditetradecanoxymethylsilane);
3-mercaptopropyl(tetradecanoxydimethylsilane);
2-mercaptoethyl(trimethoxysilane);
2-mercaptoethyl(triethoxysilane);
2-mercaptoethyl(diethoxymethoxysilane);
2-mercaptoethyl(tripropoxysilane);
2-mercaptoethyl(dipropoxymethoxysilane);
2-mercaptoethyl(tridodecanoxysilane);
2-mercaptoethyl(tritetradecanoxysilane);
2-mercaptoethyl(trihexadecanoxysilane);
2-mercaptoethyl(trioctadecanoxysilane);
2-mercaptoethyl(didodecanoxy)tetradecanoxysilane;
2-mercaptoethyl(dodecanoxy)tetradecanoxy(hexadecanoxy)silane;
2-mercaptoethyl(dimethoxymethylsilane);
2-mercaptoethyl(methoxydimethylsilane);
2-mercaptoethyl(diethoxymethylsilane);
2-mercaptoethyl(ethoxydimethylsilane);
1-mercaptomethyl(trimethoxysilane);
1-mercaptomethyl(triethoxysilane);
1-mercaptomethyl(diethoxymethoxysilane);
1-mercaptomethyl(dipropoxymethoxysilane);
1-mercaptomethyl(tripropoxysilane);
1-mercaptomethyl(trimethoxysilane);
1-mercaptomethyl(dimethoxymethylsilane);
1-mercaptomethyl(methoxydimethylsilane);
1-mercaptomethyl(diethoxymethylsilane);
1-mercaptomethyl(ethoxydimethylsilane);
1,3-dimercaptopropyl(trimethoxysilane);
1,3-dimercaptopropyl(triethoxysilane);
1,3-dimercaptopropyl(tripropoxysilane);
1,3-dimercaptopropyl(tridodecanoxysilane);
1,3-dimercaptopropyl(tritetradecanoxysilane);
1,3-dimercaptopropyl(trihexadecanoxysilane);
2,3-dimercaptopropyl(trimethoxysilane);
2,3-dimercaptopropyl(triethoxysilane);
2,3-dimercaptopropyl(tripropoxysilane);
2,3-dimercaptopropyl(tridodecanoxysilane);
2,3-dimercaptopropyl(tritetradecanoxysilane);
2,3-dimercaptopropyl(trihexadecanoxysilane);
3-mercaptobutyl(trimethoxysilane);
3-mercaptobutyl(triethoxysilane);
3-mercaptobutyl(diethoxymethoxysilane);
3-mercaptobutyl(tripropoxysilane);
3-mercaptobutyl(dipropoxymethoxysilane);
3-mercaptobutyl(dimethoxymethylsilane);
3-mercaptobutyl(diethoxymethylsilane);
3-mercaptobutyl(dimethylmethoxysilane);
3-mercaptobutyl(dimethylethoxysilane);
3-mercaptobutyl(tridodecanoxysilane);
3-mercaptobutyl(tritetradecanoxysilane);
3-mercaptobutyl(trihexadecanoxysilane);
3-mercaptobutyl(didodecanoxy)tetradecanoxysilane; or
3-mercaptobutyl(dodecanoxy)tetradecanoxy(hexadecanoxy)silane.

These compounds and others of formula I may be produced individually or mixtures of the compounds may be produced.

The (haloorganyl)alkoxysilanes compounds used in the process include those of general formula II:

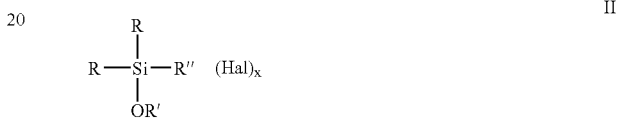

wherein x, R, R' and R" are as defined above and Hal is chlorine, bromine, fluorine or iodine. Preferred (haloorganyl)alkoxysilanes are:

3-chlorobutyl(triethoxysilane);
3-chlorobutyl(trimethoxysilane);
3-chlorobutyl(diethoxymethoxysilane);
3-chloropropyl(triethoxysilane);
3-chloropropyl(trimethoxysilane);
3-chloropropyl(diethoxymethoxysilane);
2-chloroethyl(triethoxysilane);
2-chloroethyl(trimethoxysilane);
2-chloroethyl(diethoxymethoxysilane);
1-chloromethyl(triethoxysilane);
1-chloromethyl(trimethoxysilane);
1-chloromethyl(diethoxymethoxysilane);
3-chloropropyl(diethoxymethylsilane);
3-chloropropyl(dimethoxymethylsilane);
2-chloroethyl(diethoxymethylsilane);
2-chloroethyl(dimethoxymethylsilane);
1-chloromethyl(diethoxymethylsilane);
1-chloromethyl(dimethoxymethylsilane)
3-chloropropyl(ethoxydimethylsilane);
3-chloropropyl(methoxydimethylsilane);
2-chloroethyl(ethoxydimethylsilane);
2-chloroethyl(methoxydimethylsilane);
1-chloromethyl(ethoxydimethylsilane); or
1-chloromethyl(methoxydimethylsilane).

The (haloorganyl)alkoxysilane may be a single compound of the general formula II or a mixture of compounds of the general formula II.

The (haloorganyl)halosilanes used in the process include compounds of the general formula III:

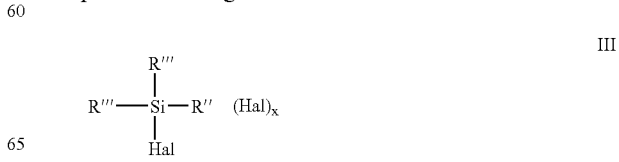

wherein x, Hal, R and R" are as defined above and the substituents R''', independently of one another, are as defined for either R or Hal above. Preferred (haloorganyl)halosilanes are:
3-chlorobutyl(trichlorosilane);
3-chloropropyl(trichlorosilane);
2-chloroethyl(trichlorosilane);
1-chloromethyl(trichlorosilane);
3-chlorobutyl(dichloromethoxysilane);
3-chloropropyl(dichloromethoxysilane);
2-chloroethyl(dichloromethoxysilane);
1-chloromethyl(dichloromethoxysilane);
3-chlorobutyl(dichloroethoxysilane);
3-chloropropyl(dichloroethoxysilane);
2-chloroethyl(dichloroethoxysilane);
1-chloromethyl(dichloroethoxysilane);
3-chlorobutyl(chlorodiethoxysilane);
3-chloropropyl(chlorodiethoxysilane);
2-chloroethyl(chlorodiethoxysilane);
1-chloromethyl(chlorodiethoxysilane);
3-chlorobutyl(chlorodimethoxysilane);
3-chloropropyl(chlorodimethoxysilane);
2-chloroethyl(chlorodimethoxysilane);
1-chloromethyl(chlorodimethoxysilane);
3-chlorobutyl(dichloromethylsilane);
3-chloropropyl(dichloromethylsilane);
2-chloroethyl(dichloromethylsilane);
1-chloromethyl(dichloromethylsilane);
3-chlorobutyl(chloro-)(methyl-)methoxysilane);
3-chloropropyl(chloro-)(methyl-)methoxysilane);
2-chloroethyl(chloro-)(methyl)-methoxysilane);
1-chloromethyl(chloro-)(methyl-)methoxysilane);
3-chlorobutyl(chloro-)(methyl-)ethoxysilane);
3-chloropropyl(chloro-)(methyl-)ethoxysilane);
2-chloroethyl(chloro-)(methyl-)ethoxysilane);
1-chloromethyl(chloro-)(methyl-)ethoxysilane);
3-chlorobutyl(chlorodimethylsilane);
3-chloropropyl(chlorodimethylsilane);
2-chloroethyl(chlorodimethylsilane); or
1-chloromethyl(chlorodimethylsilane).

The (haloorganyl)halosilane used in the process may be a single compound of formula III or a mixture of compounds of formula III.

(Mercaptoorganyl)alkoxysilanes of the general formula I:

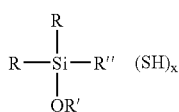

can be prepared by reacting an alkali metal sulfide with a mixture of (haloorganyl)alkoxy-silane of the general formula II:

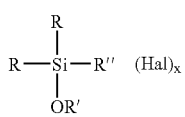

and (haloorganyl)halosilane of the general formula III:

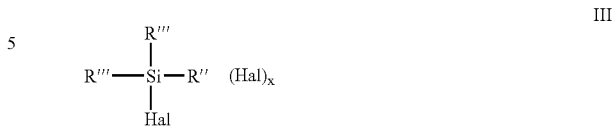

in an alcohol with the exclusion of air and under elevated pressure. The mixture of compounds produced by the process is determined by the choice of the (haloorganyl)alkoxysilanes and (haloorganyl)halosilanes.

The quality and nature of the composition of the mixture of (haloorganyl)alkoxysilane and (haloorganyl)halosilane can be evaluated on the basis of the amount and nature of the hydrolysable Si-Hal bonds contained in the mixture. This can be determined by adding 80 ml of ethanol and 10 ml of acetic acid to not more than 20 g of sample in a 150 ml glass beaker. The halide content is titrated potentiographically with a silver nitrate solution (c(AgNO3)=0.01 mol/l).

The optimum molar ratio of the mixture of (haloorganyl)alkoxysilanes and (haloorganyl)halosilanes depends, inter alia, on the number of Si-halogen functional groups of the chosen (haloorganyl)halosilanes. (Haloorganyl)alkoxysilanes and (haloorganyl)halosilanes can be used in a molar ratio of from 0.001:1 to 2:1. In the reaction of 3-chloropropyl(trimethoxysilane) or 3-chloropropyl(triethoxysilane) and 3-chloropropyl(trichlorosilane), for example, a molar ratio of from 2:1 to 2:1.5 can preferably be used, with a molar ratio of from 2:1 to 2:1.25 being still more preferable. In the reaction of 3-chloropropyl(methyldimethoxysilane) or 3-chloropropyl(methyldiethoxysilane) and 3-chloro-propyl (methyl-dichlorosilane), a molar ratio of from 1:1 to 1:1.25 can preferably be used, with a molar ratio of from 1:1 to 1:1.15 being still more preferable. In the reaction of 3-chloropropyl-(dimethylmethoxysilane) or 3-chloropropyl(dimethylethoxysilane) and 3-chloropropyl(dimethylchlorosilane), a molar ratio of from 0.001:1 to 0.05:1 can preferably be used.

The mixture of the appropriate (haloorganyl)alkoxysilane and (haloorganyl)halosilane used for the process can be prepared before the addition of the alkali sulfide, depending on the apparatus used and the desired effect, for example selectivity of the reaction, duration of the reaction, reactor coating, reactor material or process sequence.

Alkali metal sulfides may be dialkali metal sulfides, $Me_2S$, such as: dilithium sulfide ($Li_2S$); disodium sulfide ($Na_2S$); dipotassium sulfide ($K_2S$); and dicesium sulfide ($Cs_2S$). The molar amount of alkali metal sulfide used can exceed the molar amount of the (haloorganyl)halosilane by from 1% to 200%, preferably by from 1% to 150%, and more preferably by from 1% to 110%. The molar ratio of hydrolysable silicon-halogen functions in the mixtures of (haloorganyl)alkoxysilane and (haloorganyl)halosilane, to alkali metal sulfide ($Me_2S$) may be from 1:0.51 to 1:1.2, preferably from 1:0.6 to 1:1.15, and more preferably from 1:0.75 to 1:1.05.

It is possible to mix the (haloorganyl)alkoxysilane and (haloorganyl)halosilane with one another in any desired sequence and manner, at any desired temperature and for any desired duration, and only then to add the alcohol and alkali sulfide, either together or in succession. The (haloorganyl)halosilane, alkali sulfide and alcohol may be mixed with one another in any desired sequence and manner, at any desired temperature and for any desired duration, before adding the (haloorganyl)alkoxysilane. Similarly, it is possible to mix the (haloorganyl)alkoxysilane, alkali sulfide and alcohol with one another in any desired sequence and manner, at any desired temperature and for any desired duration, and only then add the (haloorganyl)halosilane.

Alcohols used in the process may be primary, secondary or tertiary alcohols having from 1 to 24, preferably from 1 to 6, and more preferably from 1 to 4, carbon atoms. Examples of alcohols include methanol, ethanol, n-propanol, isopropanol, isobutanol or n-butanol. The amount of alcohol should be at least 100 vol. %, preferably from 250 to 1000 vol. %, and more preferably from 500 to 1000 vol. %, of the silane components used.

Polar, protic, aprotic, basic or acidic additives may be added to the reaction mixture at the beginning of the reaction and/or during the reaction and/or at the end of the reaction.

The reaction can take place at temperatures of from 0 to 180° C., preferably from 50 to 150° C., and more preferably at from 70 to 120° C. The optimum reaction temperature in terms of the yield of target product and utilisation of the reaction volume can vary depending on the structure of the (haloorganyl)alkoxysilane, (haloorganyl)halosilane and alcohol used. In the case of reactions in methanol, for example, a reaction temperature of from 60 to 95° C. is advantageous with regard to reaction times, amount of secondary products and pressure build-up. In the case of reactions in ethanol, a reaction temperature of from 75 to 120° C. is advantageous.

The reaction may be carried out in a closed container under a protecting gas. It may be performed in corrosion-resistant autoclaves, for example made of glass, Teflon, enamelled or coated steel, Hastelloy or tantalum. The amount of secondary products may be kept at less than 20 mol % as a result of the choice of reaction conditions.

One advantage of the present process is that it does not require the use of a highly toxic, gaseous substance, such as hydrogen sulfide, as a sulfur donor. Instead, alkali metal sulfides, which are readily meterable solids (for example dried disodium sulfide), are used as sulfur donors. A further advantage of the process is that the selectivity of the reaction can be increased merely by using a closed reaction vessel (autoclave or the like). The process is capable of producing a high conversion in a short batch time and at a temperature that is easily achieved industrially.

EXAMPLES

Analysis by GC

The analysis by GC is carried out on a HP 6890 (WLD) gas chromatograph having a DB5 column with a thickness of 0.53 mm and a film thickness of 1.5 μm. A thermal conductivity detector is used. The temperature program used contains the following cycles:
starting temperature 100° C.
initial time 1 min.
20° C./min to 280° C.
maintain 280° C. for 10 min.

The retention times for the following components are:

| | |
|---|---|
| at 3.3 min = | Cl—$(CH_2)_3$—Si$(OEt)_3$ |
| at 5.7 min Si263 = | HS—$(CH_2)_3$—Si$(OEt)_3$ |
| at 11.0 min = | $(EtO)_3$Si—$(CH_2)_3$—S—$(CH_2)_3$—Si$(OEt)_3$ |
| at 12.4 min = | $(EtO)_3$Si—$(CH_2)_3$—$S_2$—$(CH_2)_3$—Si$(OEt)_3$ |

Example 1

29.6 g of 3-chloropropyl(triethoxysilane) and 200 ml of ethanol are together introduced at −10° C. into a stainless steel autoclave with a glass insert and a magnetic stirring device. 17.6 g of dried $Na_2S$ are added in several portions to the solution. 16.4 g of chloropropyl(trichlorosilane) are added and the autoclave is quickly closed. The autoclave and the substances therein are heated at 120° C. for 180 minutes. During that time, the pressure rises to 3.2 bar above normal pressure. The autoclave is cooled to normal temperature and the suspension that has formed is removed. The solvent contained therein is reduced in a rotary evaporator and the precipitated solid is removed using a frit that has been rendered inert. 38.4 g of a clear, slightly brownish solution are obtained. Analysis of the reaction mixture by GC shows the following composition in percent by surface area:

| | |
|---|---|
| 3-Chloropropyl(triethoxysilane) | 1.6 |
| 3-Mercaptopropyl(triethoxysilane) | 77.0 |
| $(EtO)_3$Si—$(CH_2)_3$—S—$(CH_2)_3$—Si$(OEt)_3$ | 7.3 |
| $(EtO)_3$Si—$(CH_2)_3$—$S_2$—$(CH_2)_3$—Si$(OEt)_3$ | 3.5 |

Example 2

24 g of 3-chloropropyl(triethoxysilane) and 150 ml of ethanol are together introduced at −10° C. into a stainless steel autoclave with a glass insert and a magnetic stirring device. 12 g of dried $Na_2S$ are added in several portions to the solution. 10.6 g of 3-chloropropyl(trichloros are added and the autoclave is quickly closed. The autoclave and the substances therein are heated at 80° C. for 180 minutes. The autoclave is cooled to normal temperature and the suspension that has formed is removed. The solvent contained therein is reduced in a rotary evaporator and the precipitated solid is removed using a frit that has been rendered inert. 29.2 g of a clear, slightly brownish solution are obtained. Analysis of the reaction mixture by GC shows the following composition in percent by surface area:

| | |
|---|---|
| 3-Chloropropyl(triethoxysilane) | 5.8 |
| 3-Mercaptopropyl(triethoxysilane) | 71.1 |
| $(EtO)_3$Si—$(CH_2)_3$—S—$(CH_2)_3$—Si$(OEt)_3$ | 8.4 |
| $(EtO)_3$Si—$(CH_2)_3$—$S_2$—$(CH_2)_3$—Si$(OEt)_3$ | 4.4 |

Example 3

40 g of 3-chloropropyl(triethoxysilane), 23 g of dried $Na_2S$ and 22 g of 3-chloro-propyl(trichlorosilane are together introduced at room temperature into an autoclave having a double-wall glass jacket and a stainless steel lid, and the autoclave is closed. 400 ml of ethanol are then pumped into the suspension at room temperature by means of a high-pressure pump. The mixture is heated to 80° C. and maintained at 80° C. for 5 hours. The mixture is then cooled to room temperature and analysed by gas chromatography. Analysis of the reaction mixture by GC shows the following composition in percent by weight:

| 3-Chloropropyl(triethoxysilane) | 1.3 |
|---|---|
| 3-Mercaptopropyl(triethoxysilane) | 10.3 |
| $(EtO)_3Si-(CH_2)_3-S-(CH_2)_3-Si(OEt)_3$ | 0.3 |
| $(EtO)_3Si-(CH_2)_3-S_2-(CH_2)_3-Si(OEt)_3$ | 0.9 |

Based on the above results, the selectivity is 89% and the conversion is 90%.

Example 4

40 g of 3-chloropropyl(triethoxysilane), 26.5 g of dried $Na_2S$ and 24.1 g of 3-chloropropyl(trichlorosil are together introduced at room temperature into an autoclave having a double-wall glass jacket and a stainless steel lid, and the autoclave is closed. The mixture is heated to 60° C. 400 ml of ethanol are then pumped into the suspension at 60° C. by means of a high-pressure pump. The mixture is heated further to 80° C. and maintained at 80° C. for 5 hours. The mixture is then cooled to room temperature and analysed by gas chromatography. Analysis of the reaction mixture by GC shows the following composition in percent by weight:

| 3-Chloropropyl(triethoxysilane) | 0.4 |
|---|---|
| 3-Mercaptopropyl(triethoxysilane) | 10.2 |
| $(EtO)_3Si-(CH_2)_3-S-(CH_2)_3-Si(OEt)_3$ | 1.1 |
| $(EtO)_3Si-(CH_2)_3-S_2-(CH_2)_3-Si(OEt)_3$ | 0.9 |

Based on the above components, the selectivity is 82% and the conversion is 97%.

Example 5

50 g of dried $Na_2S$ and 650 ml of dry ethanol are introduced at room temperature into an autoclave having a double-wall glass jacket and a Hastelloy C22 lid+fittings (Buechi AG). The suspension is heated and stirred at 50° C. for 20 minutes. 128.2 g of a silane mixture of 3-chloropropyl (diethoxy(chloro)silane), chloropropyl(ethoxy(dichloro)silane), chloro-propyl(trichlorosilane) and 3-chloropropyl(triethoxysilane) are added to the suspension by means of a compressed-air-operated burette. The silane mixture used is prepared by reacting 80 g of 3-chloropropyl(triethoxysilane) and 48.2 g of 3-chloropropyl(trichlorosilane). A further 150 ml of ethanol are added to the suspension by means of the burette. The mixture is heated to 97–102° C., with stirring, and the temperature is maintained for 180 minutes. The mixture is then cooled to room temperature. A sample is removed and analysed by gas chromatography. Analysis of the reaction mixture by GC shows the following composition in percent by surface area:

| 3-Chloropropyl(triethoxysilane) | 0.007 |
|---|---|
| 3-Mercaptopropyl(triethoxysilane) | 6.176 |
| $(EtO)_3Si-(CH_2)_3-S-(CH_2)_3-Si(OEt)_3$ | 0.307 |
| $(EtO)_3Si-(CH_2)_3-S_2-(CH_2)_3-Si(OEt)_3$ | 0.172 |

Based on the above values, the conversion is >99% and the selectivity of the reaction is 93%.

Example 6

50 g of dried $Na_2S$ and 650 ml of dry ethanol are introduced at room temperature into an autoclave having a double-wall glass jacket and a Hastelloy C22 lid+fittings (Buechi AG). The suspension is heated and stirred at 50° C. for 20 minutes. A mixture of 80 g of 3-chloropropyl(triethoxysilane) and 48.2 g of 3-chloropropyl(trichlorosilane) is added to the suspension by means of a compressed-air-operated burette. A further 150 ml of ethanol are added to the suspension by means of the burette. The mixture is heated to 95–100° C., with stirring, and the temperature is maintained for 180 minutes. The mixture is then cooled to room temperature. A sample is removed and analysed by gas chromatography. Analysis of the reaction mixture by GC shows the following composition in percent by surface area:

| 3-Chloropropyl(triethoxysilane) | 0.166 |
|---|---|
| 3-Mercaptopropyl(triethoxysilane) | 4.467 |
| $(EtO)_3Si-(CH_2)_3-S-(CH_2)_3-Si(OEt)_3$ | 0.276 |
| $(EtO)_3Si-(CH_2)_3-S_2-(CH_2)_3-Si(OEt)_3$ | 0.245 |

Based on the above values, the conversion is 97% and the selectivity of the reaction is 89.5%.

The reactor is emptied and flushed with a small amount of ethanol in order to remove any residues that have remained. The resulting suspension is filtered. The solid separated off is washed with 400 ml of n-pentane. The solution obtained is freed of volatile constituents at 200–600 mbar and 60–80° C. using a rotary evaporator. The suspension obtained is mixed thoroughly with 200 ml of pentane and stored for 10 hours at 4–8° C. Precipitated solid is separated off by filtration and washed with 150 ml of pentane. The pentane is removed from the resulting clear solution using a rotary evaporator at 200–600 mbar and 60–80° C. 119.3 g of a colourless liquid are obtained.

Combined analysis by GC, $^1$H-NMR and $^{29}$Si-NMR shows the following composition of the resulting product, in percent by weight:

| 3-Chloropropyl(triethoxysilane) | 2.6 |
|---|---|
| 3-Mercaptopropyl(triethoxysilane) | 84.7 |
| $(EtO)_3Si-(CH_2)_3-S-(CH_2)_3-Si(OEt)_3$ | 3.6 |
| $(EtO)_3Si-(CH_2)_3-S_2-(CH_2)_3-Si(OEt)_3$ | 5 |

Based on the above values, the conversion is 96% and the selectivity of the reaction is 91%.

Example 7

50 g of dried $Na_2S$ and 800 ml of dry ethanol are introduced at room temperature into an autoclave having a double-wall glass jacket and a Hastelloy C22 lid+fittings (Buechi AG). The suspension is heated and stirred at 50° C. for 20 minutes. A mixture of 80 g of 3-chloropropyl(triethoxysilane) and 48.2 g of 3-chloropropyl(trichlorosilane) is added to the suspension by means of a compressed-air-operated burette. A further 200 ml of ethanol are added to the suspension by means of the burette. The mixture is heated to 95–100° C., with stirring and the temperature is maintained for 180 minutes. The mixture is then cooled to room temperature. A sample is removed and analysed by gas chromatography. Analysis of the reaction mixture by GC shows the following composition in percent by surface area:

| | |
|---|---|
| 3-Chloropropyl(triethoxysilane) | 0.070 |
| 3-Mercaptopropyl(triethoxysilane) | 3.037 |
| (EtO)$_3$Si—(CH$_2$)$_3$—S—(CH$_2$)$_3$—Si(OEt)$_3$ | 0.2 |
| (EtO)$_3$Si—(CH$_2$)$_3$—S$_2$—(CH$_2$)$_3$—Si(OEt)$_3$ | 0.105 |

Based on the above values, the conversion is 98% and the selectivity of the reaction is 91%.

The reactor is emptied and flushed with a small amount of ethanol in order to remove any residues that have remained. The resulting suspension is filtered and the solid separated off is washed with 400 ml of n-pentane. The solution obtained is freed of volatile constituents at 200–600 mbar and 60–80° C. using a rotary evaporator. The resulting suspension is mixed thoroughly with 200 ml of pentane and stored for 10 hours at 4–8° C. The precipitated solid is separated off by filtration and washed with 150 ml of pentane. The pentane is removed from the resulting clear solution using a rotary evaporator at 200–600 mbar and 60–80° C. 116.2 g of a colourless liquid are obtained.

Combined analysis by GC, $^1$H-NMR and $^{29}$Si-NMR shows the following composition of the resulting product, in percent by weight:

| | |
|---|---|
| 3-Chloropropyl(triethoxysilane) | 1 |
| 3-Mercaptopropyl(triethoxysilane) | 81 |
| (EtO)$_3$Si—(CH$_2$)$_3$—S—(CH$_2$)$_3$—Si(OEt)$_3$ | 4.2 |
| (EtO)$_3$Si—(CH$_2$)$_3$—S$_2$—(CH$_2$)$_3$—Si(OEt)$_3$ | 7.1 |

Based on the above values, the conversion is 99% and the selectivity of the reaction is 88%.

Example 8

57.8 g of dried Na$_2$S and 650 ml of dry ethanol are introduced at room temperature into an autoclave having a double-wall glass jacket and a Hastelloy C22 lid+fittings (Buechi AG). The suspension is heated and stirred at 50° C. for 20 minutes. A mixture of 80.5 g of 3-chloropropyl (triethoxysilane) and 57.4 g of 3-chloropropyl(trichlorosilane) is added to the suspension by means of a compressed-air-operated burette. A further 150 ml of ethanol are added to the suspension by means of the burette. The mixture is heated to 110–115° C., with stirring, and the temperature is maintained for 120 minutes. The mixture is then cooled to room temperature. A sample is removed and analysed by gas chromatography. Analysis of the reaction mixture by GC shows the following composition in percent by surface area:

| | |
|---|---|
| 3-Chloropropyl(triethoxysilane) | 0.012 |
| 3-Mercaptopropyl(triethoxysilane) | 4.204 |
| (EtO)$_3$Si—(CH$_2$)$_3$—S—(CH$_2$)$_3$—Si(OEt)$_3$ | 0.262 |
| (EtO)$_3$Si—(CH$_2$)$_3$—S$_2$—(CH$_2$)$_3$—Si(OEt)$_3$ | 0.159 |

Based on the above-mentioned values, the conversion is >99% and the selectivity of the reaction is 91%.

The reactor is emptied and flushed with a small amount of ethanol in order to remove any residues that have remained. The resulting suspension is filtered and the solid separated off is washed with 400 ml of n-hexane. The solution obtained is freed of volatile constituents at 200–600 mbar and 60–80° C. using a rotary evaporator. The suspension obtained is mixed thoroughly with 200 ml of hexane and stored for 10 hours at 4–8° C. The precipitated solid is separated off by filtration and washed with 150 ml of hexane. The hexane is removed from the resulting clear solution using a rotary evaporator at 200–600 mbar and 60–80° C. 121.3 g of a colourless liquid are obtained.

Combined analysis by GC, $^1$H-NMR and $^{29}$Si-NMR gives the following composition of the resulting product, in percent by weight:

| | |
|---|---|
| 3-Chloropropyl(triethoxysilane) | 0.1 |
| 3-Mercaptopropyl(triethoxysilane) | 82.1 |
| (EtO)$_3$Si—(CH$_2$)$_3$—S—(CH$_2$)$_3$—Si(OEt)$_3$ | 2.3 |
| (EtO)$_3$Si—(CH$_2$)$_3$—S$_2$—(CH$_2$)$_3$—Si(OEt)$_3$ | 8.8 |

Based on the above values, the conversion is >99% and the selectivity of the reaction is 88%.

Example 9

57.7 g of dried Na$_2$S and 800 ml of dry ethanol are introduced at room temperature into an autoclave having a double-wall glass jacket and a Hastelloy C22 lid+fittings (Buechi AG). The suspension is heated and stirred at 50° C. for 20 minutes. A mixture of 80.5 g of 3-chloropropyl (triethoxysilane) and 57.4 g of 3-chloropropyl(trichlorosilane) is added to the suspension by means of a compressed-air-operated burette. A further 200 ml of ethanol are added to the suspension by means of the burette. The mixture is heated to 110–115° C., with stirring, and the temperature is maintained for 120 minutes. The mixture is then cooled to room temperature. A sample is removed and analysed by gas chromatography. Analysis of the reaction mixture by GC shows the following composition in percent by surface area:

| | |
|---|---|
| 3-Chloropropyl(triethoxysilane) | 0.007 |
| 3-Mercaptopropyl(triethoxysilane) | 3.123 |
| (EtO)$_3$Si—(CH$_2$)$_3$—S—(CH$_2$)$_3$—Si(OEt)$_3$ | 0.273 |
| (EtO)$_3$Si—(CH$_2$)$_3$—S$_2$—(CH$_2$)$_3$—Si(OEt)$_3$ | 0.154 |

Based on the above values, the conversion is >99% and the selectivity of the reaction is 88%.

The reactor is emptied and flushed with a small amount of ethanol in order to remove any residues that have remained. The resulting suspension is filtered and the solid separated off is washed with 400 ml of n-hexane. The solution obtained is freed of volatile constituents at 200–600 mbar and 60–80° C. using a rotary evaporator. The suspension obtained is mixed thoroughly with 200 ml of hexane and stored for 10 hours at 4–8° C. Precipitated solid is separated off by filtration and washed with 150 ml of hexane. The hexane is removed from the resulting clear solution using a rotary evaporator at 200–600 mbar and 60–90° C. 116.3 g of a colourless liquid are obtained.

Combined analysis by GC, $^1$H-NMR and $^{29}$Si-NMR shows the following composition of the resulting product, in percent by weight:

| | |
|---|---|
| 3-Chloropropyl(triethoxysilane) | 0.2 |
| 3-Mercaptopropyl(triethoxysilane) | 82.1 |
| (EtO)$_3$Si—(CH$_2$)$_3$—S—(CH$_2$)$_3$—Si(OEt)$_3$ | 2.4 |
| (EtO)$_3$Si—(CH$_2$)$_3$—S$_2$—(CH$_2$)$_3$—Si(OEt)$_3$ | 8.2 |

Based on the above values, the conversion is >99% and the selectivity of the reaction is 89%.

Example 10

50 g of dried $Na_2S$ and 550 ml of dry ethanol are introduced at room temperature into an autoclave having a double-wall glass jacket and a Hastelloy C22 lid+fittings (Buechi AG). The suspension is heated and stirred at 50° C. for 20 minutes. A mixture of 80 g of 3-chloropropyl(triethoxysilane) and 48.2 g of 3-chloropropyl(trichlorosilane) is added to the suspension by means of a compressed-air-operated burette. A further 150 ml of ethanol are added to the suspension by means of the burette. The mixture is heated to 112–117° C., with stirring, and the temperature is maintained for 180 minutes. The mixture is then cooled to room temperature. 1.8 g of formic acid in 50 ml of ethanol are added at 50° C. to the reaction solution by means of the pressure burette. The suspension is stirred for 15 minutes at 50° C. A sample is removed and analysed by gas chromatography. Analysis of the reaction mixture by GC shows the following composition in percent by surface area:

| | |
|---|---|
| 3-Chloropropyl(triethoxysilane) | 0.198 |
| 3-Mercaptopropyl(triethoxysilane) | 7.948 |
| $(EtO)_3Si$—$(CH_2)_3$—S—$(CH_2)_3$—$Si(OEt)_3$ | 0.368 |
| $(EtO)_3Si$—$(CH_2)_3$—$S_2$—$(CH_2)_3$—$Si(OEt)_3$ | 0.766 |

Based on the above values, the conversion is 98% and the selectivity of the reaction is 88%.

The reactor is emptied and flushed with a small amount of ethanol in order to remove any residues that have remained. The resulting suspension is filtered. The solid separated off is washed with 400 ml of n-pentane. The solution obtained is freed of volatile constituents at 200–600 mbar and 60–80° C. using a rotary evaporator. The suspension obtained is mixed thoroughly with 200 ml of pentane and stored for 10 hours at 4–8° C. The precipitated solid is separated off by filtration and washed with 150 ml of pentane. The pentane is removed from the resulting clear solution using a rotary evaporator at 200–600 mbar and 60–90° C. 124.5 g of a colourless liquid are obtained.

Combined analysis by GC, $^1$H-NMR and $^{29}$Si-NMR shows the following composition of the resulting product, in percent by weight:

| | |
|---|---|
| 3-Chloropropyl(triethoxysilane) | 2.1 |
| 3-Mercaptopropyl(triethoxysilane) | 81.5 |
| $(EtO)_3Si$—$(CH_2)_3$—S—$(CH_2)_3$—$Si(OEt)_3$ | 4.2 |
| $(EtO)_3Si$—$(CH_2)_3$—$S_2$—$(CH_2)_3$—$Si(OEt)_3$ | 10.1 |

Based on the above values, the conversion is 98% and the selectivity of the reaction is 85%.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for the preparation of (mercaptoorganyl) alkoxysilanes, comprising reacting an alkali metal sulfide with a mixture of (haloorganyl)alkoxysilane and (haloorganyl)-halosilane in an alcohol with the exclusion of air and at elevated pressure.

2. The process of claim 1, wherein a (mercaptoorganyl) alkoxysilane compound is produced of the general formula I:

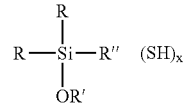

wherein the substituents R are identical or different and are selected from the group consisting of: $C_1$–$C_8$ alkyl; $C_2$–$C_{12}$ alkenyl; $C_6$–$C_{10}$ aryl; $C_7$–$C_{16}$ aralkyl; or OR', wherein the substituents R' are identical or different and are selected from the group consisting of: a $C_1$–$C_{24}$ branched or unbranched monovalent alkyl or alkenyl group; an $C_6$–$C_{10}$ aryl group; and an $C_7$–$C_{16}$ aralkyl group;

R" is a branched or unbranched, saturated or unsaturated, aliphatic, aromatic or mixed aliphatic/aromatic divalent $C_1$–$C_{30}$ hydrocarbon group which is optionally substituted by F, Cl, Br, I, $NH_2$ or NHR'; and x is 1–3.

3. The process of claim 1, wherein said (haloorganyl) alkoxysilane compounds are of the general formula II:

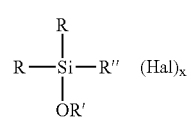

wherein the substituents R are identical or different and are selected from the group consisting of: $C_1$–$C_8$ alkyl; $C_2$–$C_{12}$ alkenyl; $C_6$–$C_{10}$ aryl; $C_7$–$C_{16}$ aralkyl; or OR', wherein the substituents R' are identical or different and are selected from the group consisting of: a $C_1$–$C_{24}$ branched or unbranched monovalent alkyl or alkenyl group; an $C_6$–$C_{10}$ aryl group; and an $C_7$–$C_{16}$ aralkyl group;

R" is a branched or unbranched, saturated or unsaturated, aliphatic, aromatic or mixed aliphatic/aromatic divalent $C_1$–$C_{30}$ hydrocarbon group which is optionally substituted by F, Cl, Br, I, $NH_2$ or NHR';

x is 1–3; and

Hal is chlorine, bromine, fluorine or iodine.

4. The process of claim 1, wherein said (haloorganyl) halosilane compounds are of the general formula III:

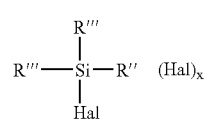

wherein R" is a branched or unbranched, saturated or unsaturated, aliphatic, aromatic or mixed aliphatic aromatic divalent $C_1$–$C_{30}$ hydrodarbon group which is optionally substituted by F, Cl, Br, I, $NH_2$, or NHR', wherein the substituent R' is selected from the group consisting of: a $C_1$–$C_{24}$ branched or unbranched monovalent alkyl or alkenyl group; an aryl group and an aralkyl group, x is 1–3; and Hal is chlorine, bromine, fluorine or iodine; and the substituents R'" are identical or different and are selected from the group consisting of: F; Cl; Br; I; $C_1$–$C_8$ alkyl; $C_2$–$C_{12}$ alkenyl; $C_6$–$C_{10}$ aryl; $C_7$–$C_{16}$ aralkyl; and OR', wherein the substituent R' is selected from the group consisting of: a $C_1$–$C_{24}$ branched or unbranched monovalent alkyl or alkenyl group; an $C_6$–$C_{10}$ aryl group; and an $C_7$–$C_{16}$ aralkyl group.

5. The process of claim 1, wherein the molar ratio of(haloorganyl)alkoxysilane to (haloorganyl)halosilane is from 0.001:1 to 2:1.

6. The process of claim 1 wherein the molar ratio of hydrolysable Si-halogen functions in the mixture of (haloorganyl)alkoxysilane and (haloorganyl)halosilane to alkali metal sulfide is from 1:0.51 to 1:1.2.

7. The process of claim 1, wherein said alkali metal sulfide is selected from the group consisting of: dilithium sulfide ($Li_2S$); disodium sulfide ($Na_2S$); and dipotassium sulfide ($K_2S$).

8. The process of claim 1, wherein said alcohol is a primary, secondary, tertiary alcohol having from 1 to 24 carbon atoms.

9. The process of claim 1, further comprising the addition of polar, protic, aprotic, basic or acidic additives to the reaction mixture at the beginning of the reaction and/or during the reaction and/or at the end of the reaction.

10. The process of claim 1, wherein said process is carried out at a temperature of from 0 to 180° C.

* * * * *